United States Patent
Ding et al.

(10) Patent No.: US 7,462,165 B2
(45) Date of Patent: *Dec. 9, 2008

(54) MEDICAL DEVICE WITH SPONGE COATING FOR CONTROLLED DRUG RELEASE

(75) Inventors: Ni Ding, Plymouth, MN (US); W. Scott Andrus, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 85 days.

This patent is subject to a terminal disclaimer.

(21) Appl. No.: 10/071,400

(22) Filed: Feb. 7, 2002

(65) Prior Publication Data

US 2002/0082552 A1    Jun. 27, 2002

Related U.S. Application Data

(62) Division of application No. 09/060,071, filed on Apr. 14, 1998, now Pat. No. 6,364,856.

(51) Int. Cl.
A61M 29/00    (2006.01)

(52) U.S. Cl. .................................. 604/103.02

(58) Field of Classification Search ............. 604/96, 604/96.01, 93.01, 99.01–99.04, 101.01–101.05, 604/103, 103.01–103.03, 103.5–103.08, 604/103.11, 103.12–103.15, 104–109, 509, 604/265, 266, 532, 285–287, 913, 920; 623/1.11, 623/1.12; 427/2.1, 2.12, 2.13, 2.22, 2.24, 427/2.25, 2.3

See application file for complete search history.

(56) References Cited

U.S. PATENT DOCUMENTS

| | | | |
|---|---|---|---|
| 4,292,965 A | 10/1981 | Nash et al. | |
| 4,299,226 A | 11/1981 | Banka | |
| 4,417,576 A * | 11/1983 | Baran | 128/207.15 |
| 4,423,725 A * | 1/1984 | Baran et al. | 128/207.15 |
| 4,603,152 A | 7/1986 | Laurin et al. | |
| 4,872,867 A | 10/1989 | Joh et al. | |
| 5,041,100 A | 8/1991 | Rowland et al. | |

(Continued)

FOREIGN PATENT DOCUMENTS

SU    1069826    1/1984

(Continued)

OTHER PUBLICATIONS

Mansoor Amiji and Kinam Park, "Surface Modification of Polymeric Biomaterials With Poly(Ethylene Oxide), Albumin, and Heparin for Reduced Thrombogenicity", Purdue University, School of Pharmacy, West Lafayette, IN, 47907.

*Primary Examiner*—Nicholas D. Lucchesi
*Assistant Examiner*—Theodore J Stigell
(74) *Attorney, Agent, or Firm*—Kenyon & Kenyon LLP (57) ABSTRACT

The medical devices of the invention comprise an expandable portion which is covered with a sponge coating for release of at least one biologically active material. The sponge coating is made of a non-hydrogel polymer having a plurality of voids. The device can further include means for infusing or expelling the biologically active material or drug into the voids. The drug is delivered to the body lumen of a patient by expelling the drug and inflating or expanding the expandable portion of the catheter or device.

7 Claims, 7 Drawing Sheets

U.S. PATENT DOCUMENTS

| | | | |
|---|---|---|---|
| 5,120,322 A | | 6/1992 | Davis et al. |
| 5,232,444 A | * | 8/1993 | Just et al. .................... 604/110 |
| 5,304,121 A | * | 4/1994 | Sahatjian ................... 604/509 |
| 5,380,299 A | | 1/1995 | Fearnot et al. |
| 5,447,724 A | * | 9/1995 | Helmus et al. .............. 604/507 |
| 5,458,568 A | * | 10/1995 | Racchini et al. ............... 604/19 |
| 5,509,899 A | | 4/1996 | Fan et al. |
| 5,545,208 A | | 8/1996 | Wolff et al. |
| 5,716,981 A | | 2/1998 | Hunter et al. |
| 6,099,562 A | * | 8/2000 | Ding et al. ................. 623/1.46 |
| 6,284,305 B1 | * | 9/2001 | Ding et al. ................. 427/2.28 |
| 6,364,856 B1 | * | 4/2002 | Ding et al. .................. 604/509 |
| 6,620,194 B2 | * | 9/2003 | Ding et al. ................. 623/1.43 |

FOREIGN PATENT DOCUMENTS

| | | |
|---|---|---|
| WO | WO 95/03083 | 7/1994 |

* cited by examiner

MEDICAL DEVICE WITH SPONGE COATING FOR CONTROLLED DRUG RELEASE

CROSS REFERENCE TO RELATED APPLICATION

This application is a divisional of application Ser. No. 09/060,071, filed Apr. 14, 1998, now U.S. Pat. No. 6,364,856, which is incorporated herein by reference in its entirety.

FIELD OF THE INVENTION

This invention relates generally to medical devices for delivering a biologically active material to a desired location within the body of a patient. More particularly, the invention is directed to medical devices having a sponge coating comprising a non-hydrogel polymer and a plurality of voids therein, optionally formed by eluting a particulate material from the polymer. The sponge coating is capable of being loaded with a drug, e.g., infusing or placing the drug into the voids, for release into the body upon expansion of the coated portion of the medical device.

BACKGROUND OF THE INVENTION

For certain diseases which are localized to a particular part of the body, the systemic administration of drugs for the treatment of these diseases may not be preferred because of the inefficiencies associated with the indirect delivery of the drugs to the afflicted area. Instead, it may be preferred that the drug be directly applied to the diseased tissue. However, such localized delivery of drugs to the walls of lumens, such as blood vessels and ducts, can be problematic since lumens are involved in the transport of body fluids, which tend to carry the drug away from the afflicted area. Thus, there is a need for devices and methods for the localized delivery of drugs to afflicted tissue, especially body lumens.

A number of methods for delivering drugs to body lumens or vessels involve the use of catheters having expandable portions, such as a balloon, disposed on the catheter. For instance, U.S. Pat. No. 5,304,121 to Sahatjian, PCT application WO 95/03083 to Sahatjian et al. and U.S. Pat. No. 5,120,322 to Davis et al. describe medical devices in which the exterior surface of the device is coated with a swellable hydrogel polymer. A solution of a drug to be delivered to the afflicted tissue is incorporated into the hydrogel. The drug is held within the matrix of the hydrogel. In the case where the medical device is a balloon catheter, the drug is delivered by inserting the catheter into the body lumen and expanding the coated balloon against the afflicted tissue of the lumen to force the drug from the hydrogel into the tissue.

However, these hydrogel coated devices have certain disadvantages. In particular, since the hydrogels are water-based, only hydrophilic drugs can be effectively incorporated into the hydrogels. Therefore, a number of useful hydrophobic biologically active materials or drugs, such as dexamethasone, cannot be suitably embedded into these hydrogels. Hence, there is a need for a coating for a medical device which can effectively incorporate such hydrophobic drugs in relatively large quantities.

Also, the application of the hydrogel coating to the balloon usually involves multiple steps because most balloon materials are hydrophobic so that a hydrogel usually has poor adhesion to the balloon surface. Another disadvantage with hydrogels is that the hydrogels will tend to be tacky or sticky when they are not fully hydrated. When a hydrogel is not in its fully hydrated state, it can stick to the surface of the packaging material or protection sheath for the coated device and make the insertion or implantation of the device difficult.

Moreover, even when prostheses having a drug containing coating are implanted into the body, it is desirable to apply a dose of the drug to the implantation site in addition to that contained in the coating. Hence, there is a need for a device which can deliver a prosthesis as well as a dose of the drug to the implantation site.

SUMMARY OF THE INVENTION

These and other objectives are accomplished by the present invention. To achieve the aforementioned objectives, we have invented a medical device and a method for making and using such device for the localized delivery of biologically active materials as well as implanted prostheses to a patient.

The medical devices of the invention comprise an expandable portion which is covered with a sponge coating for release of at least one biologically active material. The sponge coating is made of a non-hydrogel polymer having a plurality of voids. The void space of the sponge coating is greater than about 60% of the volume of the sponge coating. The device can further include means for infusing the biologically active material or drug into the voids.

In an embodiment of the invention, the device is a catheter having an expandable portion which can be inflated or expanded by inflation pressure to fill the cross-section of the body lumen and engage the tissue of the body lumen. Upon expansion, the biologically active material, which has been placed into the voids of the sponge coating, is released into the body. The catheter can also be capable of performing an angioplasty procedure at pressures of greater than 6 atm and delivering an implantable prosthesis such as a stent.

In another embodiment, the infusion means of the catheter can further comprise an inflation lumen connected to a balloon with pores. The balloon is filled with a biologically active material. When the balloon is inflated, the biologically active material infuses into the voids of the sponge coat and can be released into the body lumen.

In yet another embodiment of the present invention, a catheter has an expandable portion which comprises a reservoir defined by a porous membrane. The porous membrane or film is used to separate the sponge coating and the reservoir. The reservoir can be connected to a reservoir lumen, thereby allowing the reservoir to be filled with a biologically active material. Disposed about the porous membrane of the reservoir is a sponge coat comprising a non-hydrogel polymer having a plurality of voids formed by eluting a particulate material from the polymer. Elution of the particulate material means that such material becomes dissolved or suspended in a surrounding solvent or fluid. The catheter can further include a balloon disposed within the reservoir, wherein the balloon is connected to an inflation lumen. When the balloon is expanded the biologically active material of the reservoir is expelled or "squeezed out" through the porous membrane and infused into the voids of the sponge coat. Upon further expansion the biologically active material is released from the sponge coating into the body lumen.

Furthermore, in another embodiment of the invention the medical device, which is coated with a sponge coating is an expandable stent. The stent can be a self-expanding or balloon expandable stent.

The devices of the present invention are prepared by applying a sponge coating composition to a surface of an expandable portion of a device. The sponge coating composition comprises a non-hydrogel polymer dissolved in a solvent and an elutable particulate material. After the sponge coating composition is cured, it is exposed to a solvent, e.g., water, which causes the particulate material to elute from the polymer leaving a sponge coating having a plurality of voids therein. The sponge coating is then exposed to a biologically active material to load the sponge coating with such material. Such material may be loaded into the coating by diffusion or other means.

DESCRIPTION OF THE PREFERRED EMBODIMENTS

The medical devices suitable for the present invention include those having at least an expandable portion. Such devices include without limitation balloon catheters and perfusion catheters, which are known to the skilled artisan.

Figure 1A:
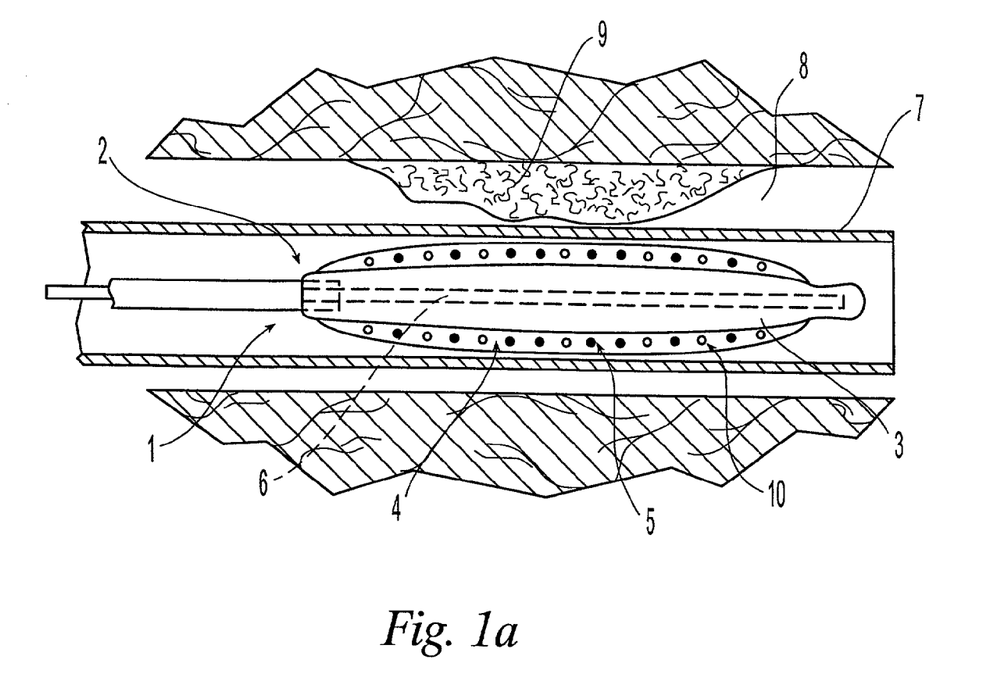
FIGS. 1a and 1b depict cross-sectional views of an embodiment of a drug delivery balloon catheter at the afflicted area of the lumen in its unexpanded and expanded state, respectively.
Figure 1B:
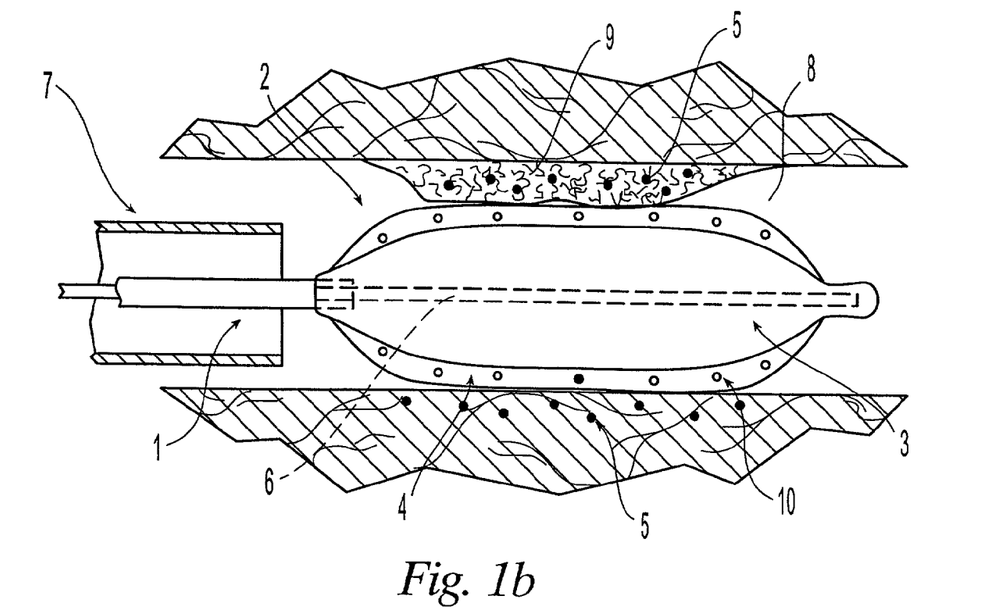

An embodiment of the present invention is illustrated in FIGS. 1a and 1b. FIG. 1a shows a catheter 1 being delivered to the afflicted tissue 9 of a body lumen 8. The catheter 1 comprises an expandable portion 2 having a balloon 3 disposed about the catheter 1. The outer surface of the balloon 3 is covered with a sponge coating 4 of a non-hydrogel polymer having a plurality of voids 10 therein. A drug 5 is placed into the voids 10. An inflation lumen 6 is connected to the balloon 3 to fill the balloon 3 with fluid, such as a liquid, or pressurized gas, and to expand the balloon 3. A protective sheath 7 can be placed around the expandable portion 2 to prevent the drug 5 from being inadvertently released during insertion of the catheter 1 into the body lumen 8.

FIG. 1b shows the catheter 1 in its deployed state. In FIG. 1b, the balloon 3 has been expanded to deliver the drug 5. The drug 5 is forced out of the sponge coating 4 by the expansion of the balloon 3 against the body lumen 8. The drug 5 is thereby released into the afflicted tissue 9 for treatment. In the case of an expanded balloon, as shown in FIG. 1b, the expansion of the balloon causes the sponge coating layer to become thinner, resulting in an expulsion of the drug from the coating 4.

Figure 2A:
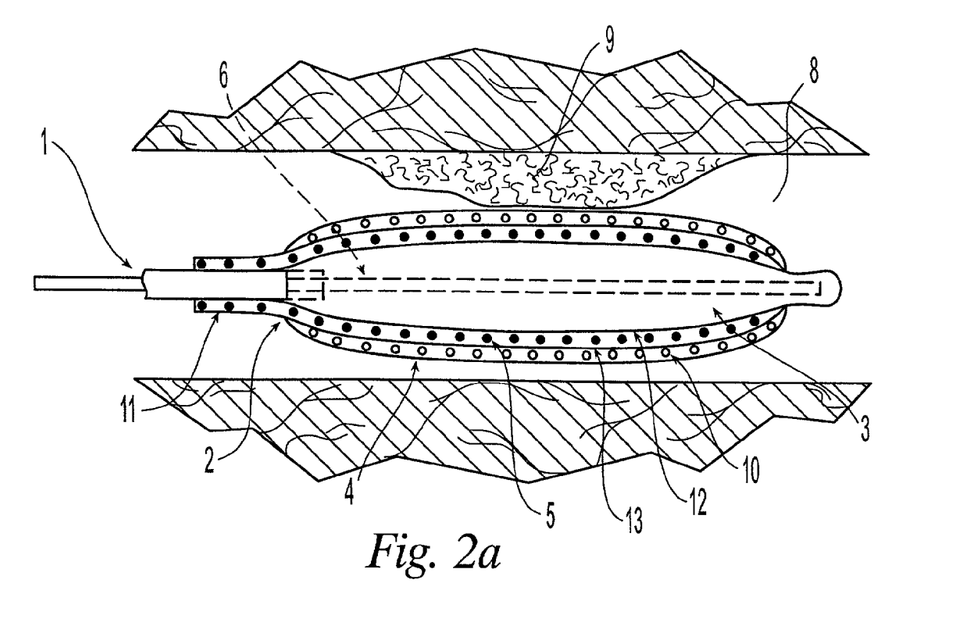
FIGS. 2a and 2b depict cross-sectional views of an embodiment of a drug delivery catheter having a drug reservoir in its unexpanded and expanded state, respectively.
Figure 2B:
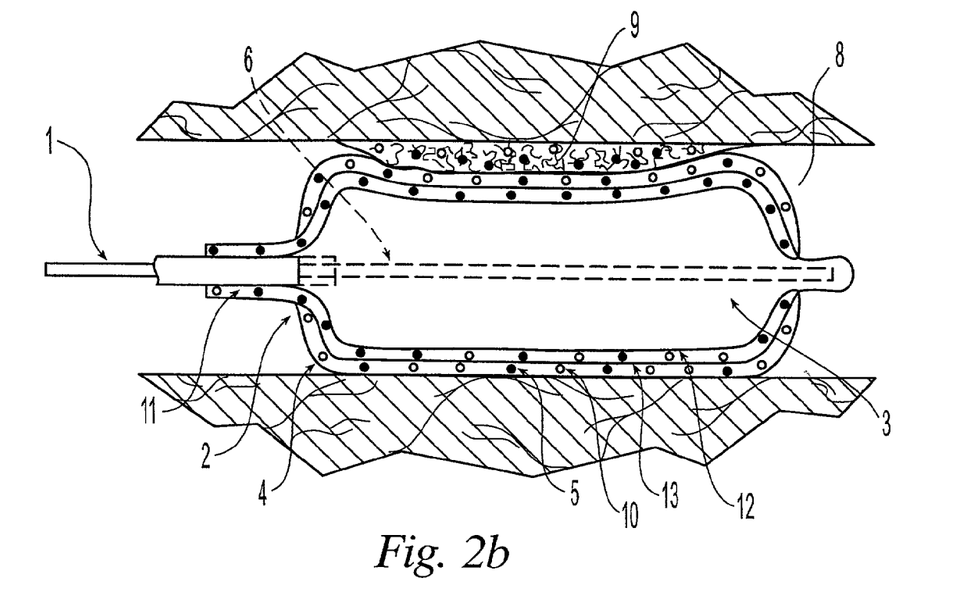
Figure 2C:
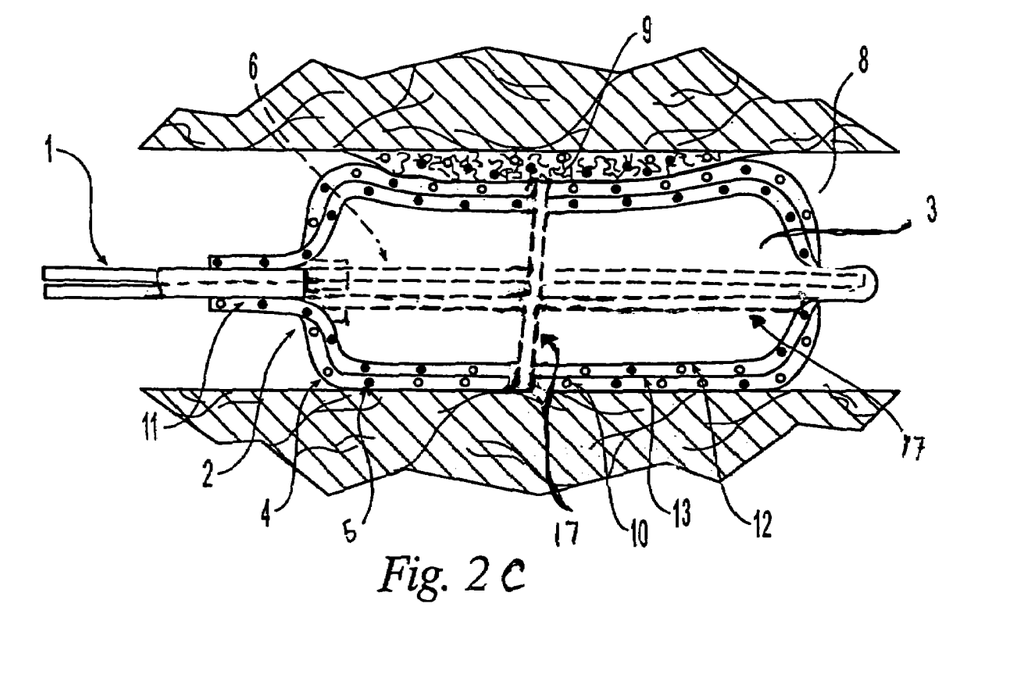

Another embodiment of the invention is depicted in FIGS. 2a and 2b. The catheter 1 of this embodiment comprises an expandable portion 2 having a reservoir 12 disposed about a balloon 3 connected to an inflation lumen 6. The reservoir 12 is connected to a reservoir lumen 11 which can be used to fill the reservoir 12 with the drug 5. A porous membrane 13 defines the reservoir's outer surface. A sponge coating 4—having voids 10 therein covers the outer surface of the reservoir 12, i.e., outside the porous membrane 13.

The drug 5 is delivered to the afflicted tissue 9 by filling the reservoir 12 through the reservoir lumen 11 with a drug 5. As the balloon 3 is expanded, drug 5 in the reservoir 12 passes or is forced through the porous membrane 13 into the voids 10 of the sponge coating 4. Additional expansion of the balloon 3 causes the drug 5, which is in the sponge coating 4 to be released from the sponge coating 4 into the afflicted tissue 9. A perfusion lumen can be included in the catheter 1 to sustain the inflation of the balloon 3 and infusion of the drug 5 into the sponge coating 4.

One of the advantages of infusing the sponge coating with the drug is that such infusion maximizes the amount of drug delivered to the afflicted area of the body lumen and reduces the amount of drug which is lost to the lumen fluid, e.g., blood. Also, infusion of the sponge coating with the drug permits the more even distribution of the drug onto the afflicted lumen tissue without damaging such tissue.

Also, a control unit (not shown) can be included to synchronize the inflation of the balloon 3 with the delivery of the drug 5 and the deflation of the balloon 3 with the infusion of the drug 5 into the sponge coating 4. Such a control unit would manipulate the timing of the infusion of the drug 5 into the sponge coating 4 when the balloon 3 is being deflated instead of when it is being inflated. Synchronization of—infusion with deflation minimizes undesired "jetting" or excess release of large quantities of drug 5 into the body lumen.

Figure 3:
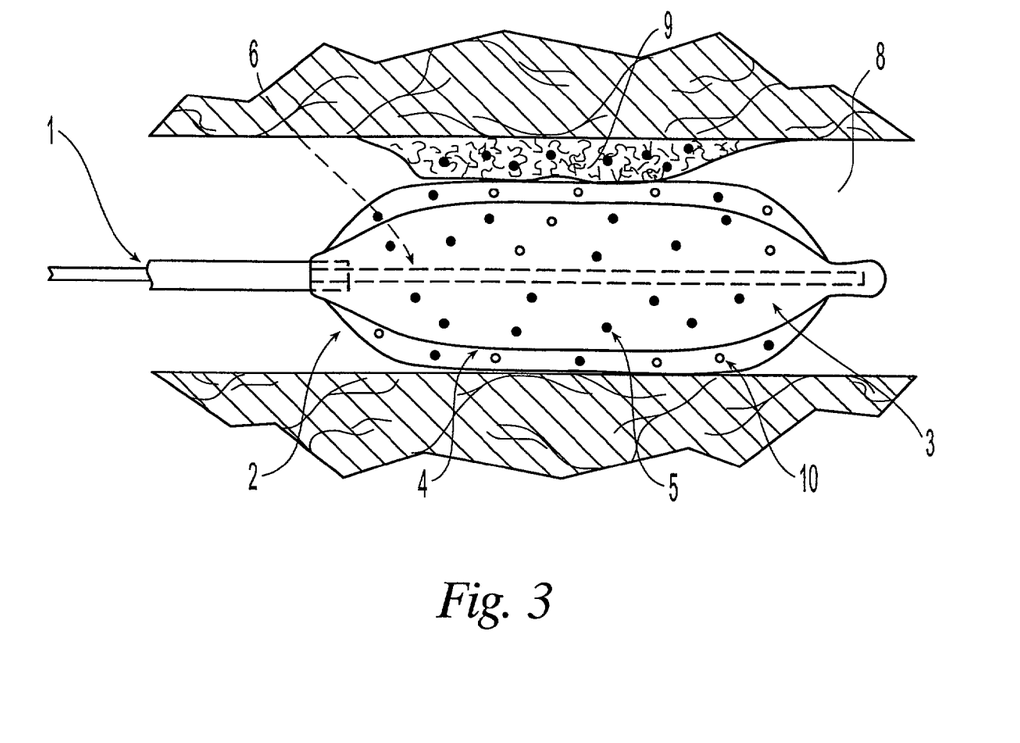
FIG. 3 depicts a cross-sectional view of an embodiment of a drug delivery catheter having a balloon containing a drug in its expanded state.

FIG. 3 illustrates yet another embodiment of a catheter 1 in its expanded state wherein the balloon 3 and reservoir 12 of the embodiment of FIGS. 2a and 2b are combined. In this embodiment, drug 5 is placed into the balloon 3 through the inflation lumen 6 to expand the balloon 3. In other words by filling the balloon 3 with a fluid or composition containing the drug 5, the balloon 3 is expanded. The force of expansion causes the drug 5 in the balloon 3 to infuse the drug 5 into the voids 10 of the sponge coating 4. By expanding the balloon 3 further the drug 5 can be released from the sponge coating 4 into afflicted tissue 9.

In addition, the catheters of the invention can be used to deliver an implantable prosthesis such as an expandable stent. The expandable stents which can be used in this invention include self-expanding stents and balloon expandable stents. Examples of self-expanding stents useful in the present invention are illustrated in U.S. Pat. Nos. 4,655,771 and 4,954,126 issued to Wallsten and 5,061,275 issued to Wallsten et al. Examples of appropriate balloon-expandable stents are shown in U.S. Pat. No. 4,733,665 issued to Palmaz, U.S. Pat. No. 4,800,882 issued to Gianturco and U.S. Pat. No. 4,886,062 issued to Wiktor.

Since the stent is implanted in the body, it can be covered with a drug-releasing coating which provides long term delivery of the drug. Generally, these coatings comprise a drug incorporated into a polymeric material. Such drug-releasing coatings are described in U.S. Pat. No. 5,464,650 to Berg et al.

The expandable stent may be formed from polymeric, metallic and/or ceramic materials. Suitable polymeric materials include without limitation poly-L-lactic acid, polycarbonate, and polyethylene terephthalate.

Figure 4A:
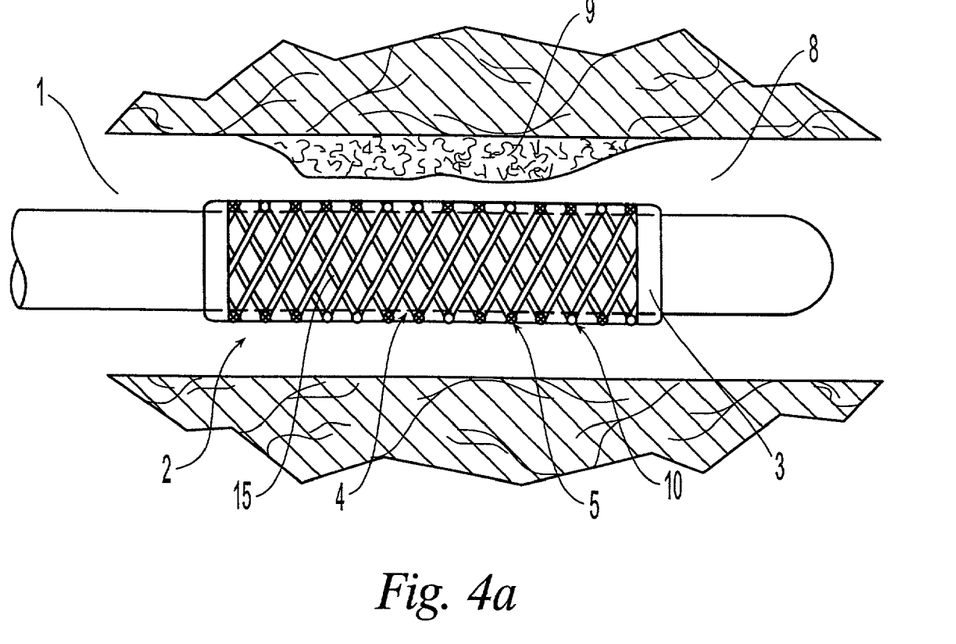
FIGS. 4a and 4b depict a balloon expandable stent prosthesis, in its unexpanded and expanded state respectively, which is mounted on an expandable portion of a drug delivery catheter.
Figure 4B:
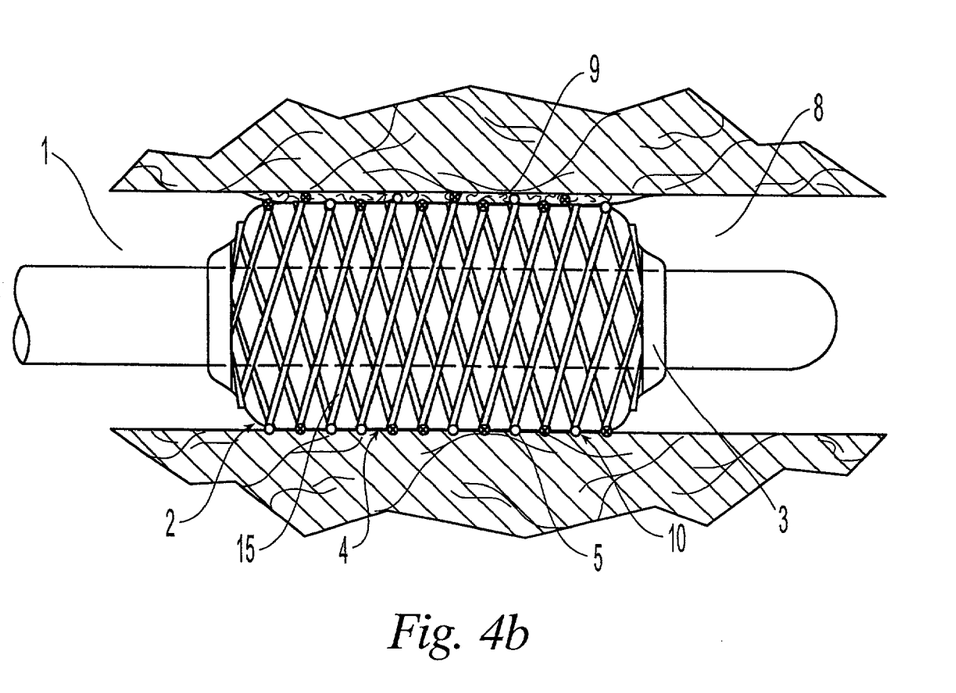

FIGS. 4a and 4b show the delivery and deployment of a balloon expandable stent 15 by a catheter 1 coated with a sponge coating 4 having a drug 5 infused into the voids 10 of the sponge coating 4. The stent 15 is disposed on the expandable portion 2 of the catheter 1 for delivery as in FIG. 4a. The stent can also be coated with a sponge coating, particularly one where the particulate material is a drug. The stent 15 is implanted by expanding the balloon 3 to force open the stent.

Also, as shown in FIG. 4b, when the stent 15 is deployed, expansion of the balloon 3 causes the drug 5 to infuse into the voids 10 of the sponge coating 4 and to be released into the body lumen 8.

Figure 5A:
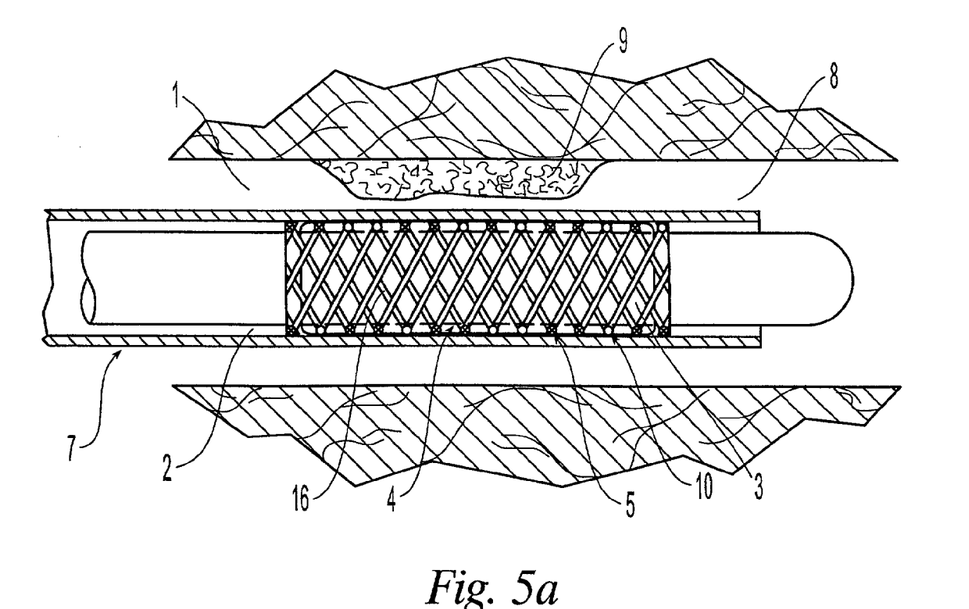
FIGS. 5a and 5b depict a self-expanding stent prosthesis, in its unexpanded and expanded state respectively, which is mounted on an expandable portion of a drug delivery catheter.
Figure 5B:
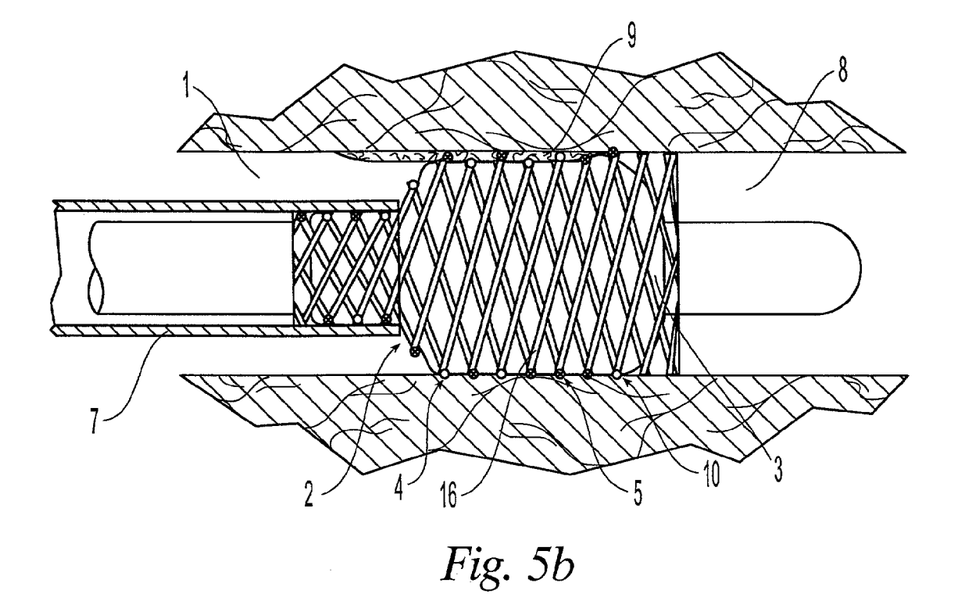

The delivery and deployment of a self-expanding stent 16 by a coated catheter 1 of the present invention is illustrated in FIGS. 5a and 5b. In FIG. 5a, a sheath 7 is placed around the stent 16, which is disposed about the expandable portion 2 of the catheter 1, to maintain the stent 16 in a contracted state for delivery. After the stent 16 is placed to its implantation site, the sheath 7 is withdrawn to deploy the self-expanding stent 16. While or after the stent 16 expands, the balloon 3 is expanded to further dilate the stent and release the drug 5 from the sponge coating 4.

The following is a more detailed description of suitable materials and methods useful in producing the sponge coatings of the invention.

The non-hydrogel polymer(s) useful for forming the sponge coating should be ones that are biostable, biocompatible, particularly during insertion or implantation of the device into the body and avoids irritation to body tissue. Non-hydrogel polymers are polymers that when a drop of water is added on top of a film of such polymer, the drop will not spread. Examples of such polymers include without limitation polyurethanes, polyisobutylene and its copolymers, silicones, and polyesters. Other suitable polymers include polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate, copolymers of vinyl-monomers, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers.

Since the polymer is being applied to a part of the medical device which undergoes mechanical challenges, e.g., expansion and contraction, the polymers are preferably selected from elastomeric polymers such as silicones (e.g. polysiloxanes and substituted polysiloxanes), polyurethanes, thermoplastic elastomers, ethylene vinyl acetate copolymers, polyolefin elastomers, polyisobutylene and its copolymers and EPDM rubbers. The polymer is selected to allow the coating to better adhere to the surface of the expandable portion of the medical device when it is subjected to forces or stress.

Furthermore, although the sponge coating can be formed by using a single type of polymer, various combinations of polymers can be employed. The appropriate mixture of polymers can be coordinated with biologically active materials of interest to produce desired effects when coated on a medical device in accordance with the invention.

The elutable particulate materials which can be incorporated into the polymer include without limitation polyethylene oxide, polyethylene glycol, polyethylene oxide/polypropylene oxide copolymers, polyhydroxyethyl methacrylate, polyvinylpyrrolidone, polyacrylamide and its copolymers, salts, e.g., sodium chloride, sugars, and elutable biologically active materials such as heparin.

The amount of elutable particulate material that is incorporated into the polymer should range from about 20% to 90% by weight of the sponge coating and preferably, from about 50% to 90%. The average particle size of the elutable material can range from 1-100 microns and preferably from about 2 to 15 microns.

The solvent that is used to form the mixture or slurry of polymer and elutable particulate materials includes ones which can dissolve the polymer into solution and do not alter or adversely impact the therapeutic properties of the biologically active material employed. Examples of useful solvents for silicone include tetrahydrofuran (THF), chloroform and dichloromethane.

The composition of polymer and elutable particulate material can be applied to the expandable portion of the medical device in a variety of ways. For example, the composition can be spraycoated onto the device or the device can be dipped into the composition. One of skill in the art would be aware of methods for applying the coating to the device. The thickness of the sponge coating can range from about 25 μm to 0.5 mm. Preferably, the thickness is about 30 μm to 100 μm.

After the composition is applied to the device, it should be cured to produce a polymer containing the particulate material and to evaporate the solvent. Certain polymers, such as silicone, can be cured at relatively low temperatures (e.g. room temperature) in what is known as a room temperature vulcanization (RTV) process. More typically, the curing/evaporation process involves higher temperatures so that the coated device is heated in a oven. Typically, the heating occurs at approximately 90° C. or higher for approximately 1 to 16 hours when silicone is used. For certain coatings the heating may occur at temperatures as high as 150° C. The time and temperature of heating will of course vary with the particular polymer, drugs, and solvents used. One of skill in the art is aware of the necessary adjustments to these parameters.

To elute the particulate material from the polymer, a solvent is used. The device can be soaked in the solvent to elute the particulate materials. Other methods of eluting the particulate are apparent to those skilled in the art.

The choice of the solvent depends upon the solubility of the elutable particulate material in that solvent. For instance, for water-soluble particulate materials such as heparin, water can be used. For elutable particulate materials that can be dissolved in organic solvents, such organic solvents can be used. Examples of suitable solvents, without limitation, include ethanol, dimethyl sulfoxide, etc.

After the particulate material is eluted from the polymer, the medical device can be optionally sterilized. Depending upon the nature of the drug used, sterilization of the device can occur before or after the drug is loaded into the sponge coating. Methods of sterilization are known in the art. For example, the devices can be sterilized by exposure to gamma radiation at 2.5-3.5 Mrad or by exposure to ethylene oxide.

Figure 6A:
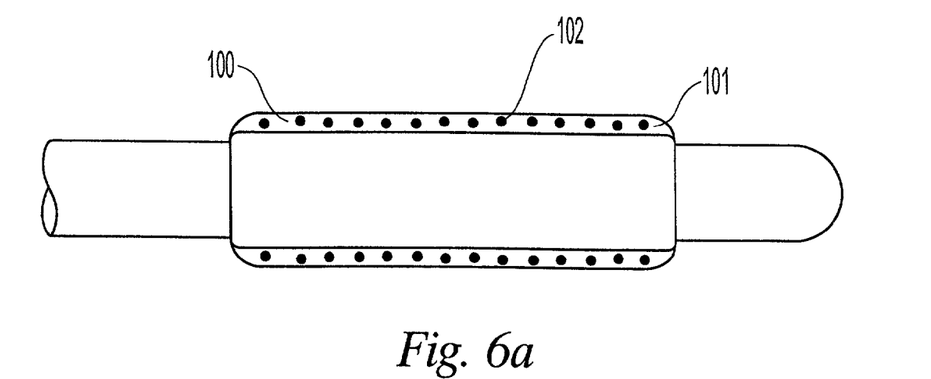
FIGS. 6a-6c depict a method of preparing the sponge coating for a balloon catheter.
Figure 6B:
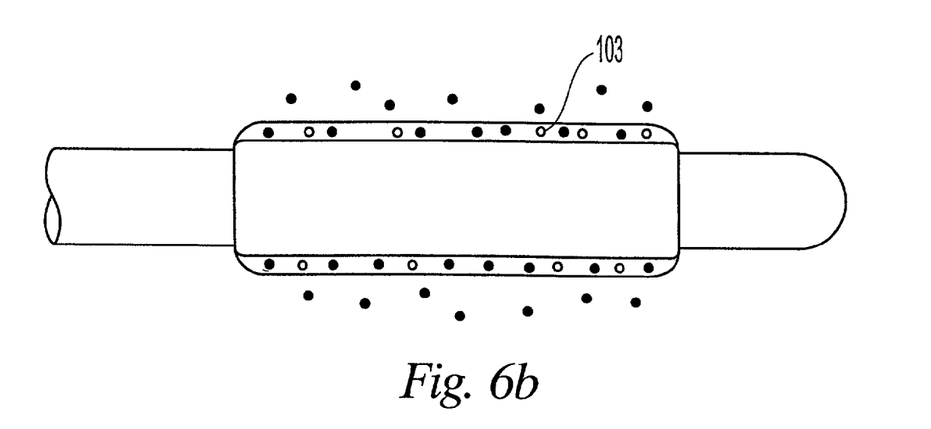
Figure 6C:
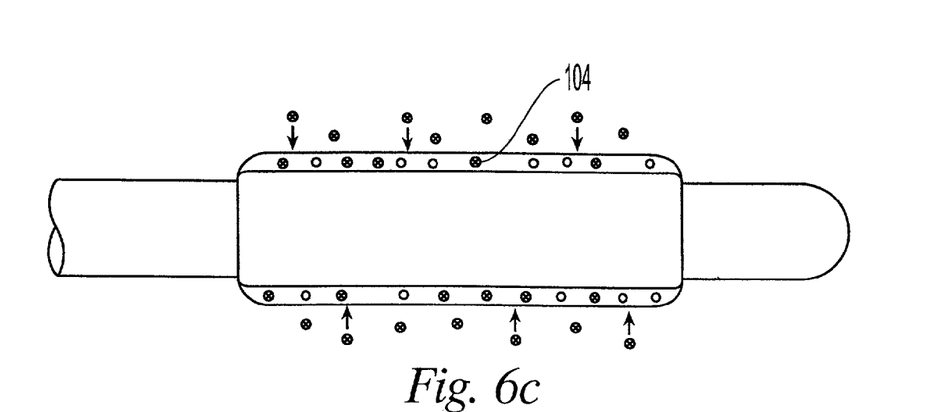

As shown in FIGS. 6a-6c, in one method for making the sponge coating 100, a mixture or slurry comprising a non-hydrogel polymer 101, an elutable particulate material 102 and a solvent is applied to an expandable portion of the medical device. The device is then exposed to an aqueous or organic solvent to elute the particulate material 102 from the polymer 101 to form a plurality of voids 103 in the polymer 101. A biologically active material or drug 104 is then loaded or placed into the voids 103 prior to delivery of the drug 104 to the body.

To load the sponge coating with the biologically active material or drug, a composition comprising the drug is applied to the sponge coating. The drug can be loaded just prior to use of the medical device. The drug can be loaded by immersing the sponge coated portion of the device into the drug solution and allowing the drug to diffuse into the voids of the sponge coating.

In order to place or infuse the drug into the sponge coating, the drug should be dissolved or dispersed into a solvent. The sponge coated portion of the device is then immersed into the drug solution. Due to diffusion, the drug will enter the voids of the sponge coating. After the solvent is permitted to evaporate, a drug coated device is formed. The device can then be sterilized. If the drug can not be sterilized, the physician can load the drug just before the insertion or implantation procedure is performed.

Alternatively, the medical device can be constructed such that the drug can be infused from within the medical device as described in the above-mentioned embodiments. For instance, the catheter can include a drug reservoir whereby inflation of the balloon causes the drug in the reservoir to infuse into the sponge coating.

Furthermore, in another method for making the sponge coating, the coating can be formed in vivo, i.e., while the device, which is coated with a polymer and an elutable particulate material, is, inserted or implanted in the body. To prepare such a coating, particulates, e.g., hydrophilic or lipophobic drug particles are mixed with non-hydrogel polymeric materials. The surface of the expandable portion of the medical device, such as a balloon, is then coated with this mixture. After the coated device is implanted or inserted into the body, body fluid which contacts the coating permeates into the coating, thereby swelling the coating and dissolving the drug. Some of the drug is then eluted into the body fluid. When the balloon is inflated, additional drug is forced out from the coating and directed to the afflicted body lumen. In such a manner, a significant quantity of drug can be delivered to the body lumen.

Suitable biologically active materials that can be used in this invention include without limitation glucocorticoids (e.g. dexamethasone, betamethasone), heparin, hirudin, angiopeptin, aspirin, growth factors, antisense agents, anti-cancer agents, anti-proliferative agents, oligonucleotides, and, more generally, antiplatelet agents, anti-coagulant agents, antimitotic agents, antioxidants, anti-metabolite agents, and anti-inflammatory agents could be used. Antiplatelet agents can include drugs such as aspirin and dipyridamole. Aspirin is classified as an analgesic, antipyretic, anti-inflammatory and—antiplatelet drug. Dipyridamole is a drug similar to aspirin in that it has anti-platelet characteristics. Dipyridamole is also classified as a coronary vasodilator. Anticoagulant agents can include drugs such as heparin, protamine, hirudin and tick anticoagulant protein. Anti-cancer agents can induce drugs such as taxol, and its analogs or derivatives, antioxidant agents can include probucol. Anti-proliferative agents can include drugs such as amlodipine and doxazosin. Antimitotic agents and antimetabolite agents can include drugs such as methotrexate, azathioprine, vincristine, vinblastine, 5-fluorouracil, adriamycin and mutamycin. Antibiotic agents can include penicillin, cefoxitin, oxacillin, tobramycin, and gentamicin. Suitable antioxidants include probucol. Also, genes or nucleic acids, or portions thereof can be used. Such genes or nucleic acids can first be packaged in liposomes or nanoparticles. Furthermore, collagen-synthesis inhibitors, such as tranilast, can be used.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

We claim:

1. A catheter for delivering a biologically active material to a desired location of a body lumen of a patient comprising an expandable portion which is insertable or implantable into a body lumen, wherein the expandable portion is expandable in response to inflation pressure to fill the cross-section of the lumen and engage the tissue of the lumen and wherein the expandable portion comprises:
    a) a balloon having an outer surface;
    b) a membrane having a plurality of pores therein wherein the membrane comprises an outer surface and an inner surface, wherein the membrane is disposed about the balloon;
    c) a reservoir space disposed between the outer surface of the balloon, and the inner surface of the membrane and wherein the reservoir space is connected to a reservoir lumen for filling the reservoir space with the biologically active material; and
    d) a biostable sponge coating disposed upon the outer surface of the membrane wherein the sponge coating is exposed to the body lumen when the catheter is inserted or implanted into the body lumen and, wherein the sponge coating comprises a non-hydrogel polymer having a plurality of voids and wherein the sponge coating is in fluid communication with the reservoir space such that the biologically active material when present in the reservoir space can pass through the pores of the membrane and enter the voids.

2. The catheter of claim 1 wherein the voids are formed by eluting a particulate material from the polymer.

3. The catheter of claim 1, wherein the void space of the sponge coating is greater than about 60% of the volume of the sponge coating.

4. The catheter of claim 1 further comprising an inflation lumen connected to the balloon.

5. The catheter of claim 1 wherein the polymer comprises an elastomer.

6. The catheter of claim 5 wherein the elastomer comprises a silicone, polyurethane, thermoplastic elastomer, ethylene vinyl acetate copolymer, polyolefin elastomer, or EPDM rubber.

7. The catheter of claim 1 wherein the biologically active material is heparin, paclitaxel, or rapamycin.

\* \* \* \* \*

UNITED STATES PATENT AND TRADEMARK OFFICE
CERTIFICATE OF CORRECTION

PATENT NO. : 7,462,165 B2  Page 1 of 1
APPLICATION NO. : 10/071400
DATED : December 9, 2008
INVENTOR(S) : Ding et al.

It is certified that error appears in the above-identified patent and that said Letters Patent is hereby corrected as shown below:

Column 8, line 31 (claim 1, line 17), "active material;" should be changed to
--active material, the reservoir space extending substantially the length of the balloon;--.

Signed and Sealed this

Twentieth Day of October, 2009

David J. Kappos
*Director of the United States Patent and Trademark Office*